United States Patent
Hewitt et al.

(10) Patent No.: US 10,203,796 B2
(45) Date of Patent: Feb. 12, 2019

(54) TOUCH PREDICTION FOR VISUAL DISPLAYS

(71) Applicant: International Business Machines Corporation, Armonk, NY (US)

(72) Inventors: Trudy L. Hewitt, Cary, NC (US); Debra J. McKinney, Semora, NC (US); Christina L. Wetli, Raleigh, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/191,680

(22) Filed: Jun. 24, 2016

(65) Prior Publication Data

US 2016/0306494 A1    Oct. 20, 2016

Related U.S. Application Data

(63) Continuation of application No. 14/295,401, filed on Jun. 4, 2014, now Pat. No. 9,406,025.

(51) Int. Cl.
*G06F 3/041* (2006.01)
*G06F 3/0488* (2013.01)
(Continued)

(52) U.S. Cl.
CPC .......... *G06F 3/0416* (2013.01); *G06F 3/0488* (2013.01); *G06F 3/04883* (2013.01);
(Continued)

(58) Field of Classification Search
CPC .... G06F 3/017; G06F 3/04883; G06F 3/0487; G06F 3/0488; G06F 3/04886; G06F 2203/04808
See application file for complete search history.

(56) References Cited

U.S. PATENT DOCUMENTS 6,256,021 B1 * 7/2001 Singh .................... G06F 3/0418
                                                        345/173
6,931,384 B1 * 8/2005 Horvitz .................. G06N 7/005
                                                        704/E15.026
(Continued)

FOREIGN PATENT DOCUMENTS

WO    2007139484 A1    12/2007

OTHER PUBLICATIONS

Lettner et al., "Heat maps as a usability tool for multi-touch interaction in mobile applications," Proceedings of the 11th International Conference on Mobile and Ubiquitous Multimedia, Article No. 49, Dec. 4-6, 2012, Ulm, Germany, 2 pages doi: 10.1145/2406367.2406427.

(Continued)

*Primary Examiner* — William Lu
(74) *Attorney, Agent, or Firm* — Peter J. Edwards

(57) ABSTRACT

Touch events can be predicted relative to a visual display by maintaining a database of aggregated touch event history data relative to the visual display and from a plurality of touch screen devices. The database can be queried according to a set of input parameters defining an environment for use of the visual display. The results from the querying of the database can be analyzed to predict a set of touch events within the environment and based upon inferences obtained from the results. A representation of the set of touch events can be displayed along with the visual display.

15 Claims, 9 Drawing Sheets

(51) Int. Cl.
  *G06F 17/30* (2006.01)
  *G06N 7/00* (2006.01)
  *G16H 40/63* (2018.01)
  *G06N 5/04* (2006.01)
  *G06F 19/00* (2018.01)

(52) U.S. Cl.
  CPC ........ *G06F 17/30554* (2013.01); *G06F 19/00* (2013.01); *G06N 5/04* (2013.01); *G06N 7/005* (2013.01); *G16H 40/63* (2018.01); *G06F 2203/04104* (2013.01); *G06F 2203/04808* (2013.01)

(56) References Cited

U.S. PATENT DOCUMENTS

| | | | |
|---|---|---|---|
| 7,483,692 B2 | 1/2009 | Zak et al. | |
| 7,941,525 B1 * | 5/2011 | Yavilevich | H04L 67/22 709/203 |
| 8,289,295 B2 | 10/2012 | Chou | |
| 8,373,669 B2 * | 2/2013 | Miernik | G06F 3/0416 345/169 |
| 8,570,294 B2 | 10/2013 | Adamson et al. | |
| 8,706,827 B1 | 4/2014 | Noble et al. | |
| 8,831,754 B2 | 9/2014 | Taylor et al. | |
| 9,144,905 B1 * | 9/2015 | Sinapov | B25J 9/1671 |
| 9,218,083 B2 | 12/2015 | Tseng et al. | |
| 9,286,081 B2 * | 3/2016 | Dunn | G06F 9/4443 |
| 9,372,577 B2 * | 6/2016 | Zafiris | G06F 3/0418 |
| 9,703,473 B2 * | 7/2017 | Schillings | G06F 3/04883 |
| 2002/0054090 A1 * | 5/2002 | Silva | G06F 17/30905 715/747 |
| 2004/0056845 A1 | 3/2004 | Harkcom et al. | |
| 2006/0036462 A1 | 2/2006 | King et al. | |
| 2006/0136385 A1 | 6/2006 | Bobrow et al. | |
| 2006/0173712 A1 | 8/2006 | Joubert | |
| 2007/0165924 A1 | 7/2007 | Nicponski | |
| 2007/0239535 A1 | 10/2007 | Koran et al. | |
| 2007/0271573 A1 | 11/2007 | Chandrasekaran | |
| 2008/0253757 A1 | 10/2008 | Bells et al. | |
| 2008/0274798 A1 | 11/2008 | Walker et al. | |
| 2009/0104954 A1 | 4/2009 | Weber et al. | |
| 2009/0106225 A1 | 4/2009 | Smith et al. | |
| 2009/0112608 A1 | 4/2009 | Abu-Hakima et al. | |
| 2009/0167542 A1 | 7/2009 | Culbert et al. | |
| 2010/0153890 A1 * | 6/2010 | Wang | G06F 3/011 715/863 |
| 2010/0238125 A1 * | 9/2010 | Ronkainen | G06F 3/04886 345/173 |
| 2010/0274804 A1 | 10/2010 | Muskal et al. | |
| 2010/0280988 A1 | 11/2010 | Underkoffler et al. | |
| 2010/0293106 A1 | 11/2010 | Rhoads et al. | |
| 2010/0306709 A1 * | 12/2010 | Lynch | G06F 17/30516 715/854 |
| 2011/0141144 A1 | 6/2011 | Tomono | |
| 2011/0238612 A1 * | 9/2011 | Wilson | G06F 3/0481 706/52 |
| 2011/0302488 A1 | 12/2011 | Lee et al. | |
| 2012/0016621 A1 | 1/2012 | Tan et al. | |
| 2012/0154324 A1 * | 6/2012 | Wright | G06F 3/0416 345/174 |
| 2012/0169646 A1 * | 7/2012 | Berkes | G06F 3/0488 345/174 |
| 2012/0206380 A1 * | 8/2012 | Zhao | G06F 3/04883 345/173 |
| 2012/0310687 A1 | 12/2012 | Carter | |
| 2013/0074051 A1 | 3/2013 | Freeman | |
| 2013/0080891 A1 | 3/2013 | Byun | |
| 2013/0096991 A1 | 4/2013 | Gardner et al. | |
| 2013/0121580 A1 | 5/2013 | Chen et al. | |
| 2013/0132833 A1 | 5/2013 | White et al. | |
| 2013/0132856 A1 | 5/2013 | Binyamin et al. | |
| 2013/0135218 A1 * | 5/2013 | Jain | G06F 3/0488 345/173 |
| 2013/0152002 A1 | 6/2013 | Menczel et al. | |
| 2013/0227476 A1 * | 8/2013 | Frey | G06F 3/0488 715/810 |
| 2013/0262935 A1 * | 10/2013 | Kutchuk | G06F 11/3438 714/39 |
| 2013/0304906 A1 * | 11/2013 | Yavilevich | H04L 67/22 709/224 |
| 2013/0346922 A1 * | 12/2013 | Shiplacoff | G06F 3/04842 715/835 |
| 2014/0053260 A1 | 2/2014 | Gupta et al. | |
| 2014/0108994 A1 | 4/2014 | Medlock et al. | |
| 2014/0132571 A1 | 5/2014 | Zeng et al. | |
| 2014/0139556 A1 | 5/2014 | Pan | |
| 2014/0173418 A1 * | 6/2014 | Seifert | G06F 17/24 715/234 |
| 2014/0204036 A1 | 7/2014 | Schillings et al. | |
| 2014/0244744 A1 | 8/2014 | Lyren | |
| 2014/0310335 A1 * | 10/2014 | Snibbe | H04L 67/38 709/203 |
| 2014/0358825 A1 | 12/2014 | Phillipps et al. | |
| 2015/0082135 A1 | 3/2015 | Schlesinger et al. | |
| 2015/0169142 A1 | 6/2015 | Longo et al. | |
| 2015/0227258 A1 | 8/2015 | Wang et al. | |
| 2015/0234454 A1 | 8/2015 | Kurz | |
| 2015/0332158 A1 * | 11/2015 | He | G06N 7/005 706/52 |
| 2015/0355772 A1 | 12/2015 | Hewitt et al. | |
| 2016/0012855 A1 * | 1/2016 | Krishnan | G11B 27/105 386/241 |
| 2016/0103555 A1 | 4/2016 | Hewitt et al. | |

OTHER PUBLICATIONS

Mell et al., "The NIST Definition of Cloud Computing," National Institute of Standards and Technology, U.S. Department of Commerce, Special Publication 800-145, Sep. 2011, 7 pages.

Unknown, "Visualize users every touch with heat maps," Heatmaps, https://heatmaps.io/, 5 pages.

U.S. Appl. No. 14/977,786, Accelerated Examination Support Document, Dated Dec. 15, 2015, 5 pages.

List of IBM Patents or Patent Applications Treated as Related, Jun. 23, 2016, 2 pages.

Hewitt et al., "Touch Prediction for Visual Displays," U.S. Appl. No. 15/191,668, filed Jun. 24, 2016.

Hewitt et al., "Touch Prediction for Visual Displays," U.S. Appl. No. 15/191,694, filed Jun. 24, 2016.

Hewitt et al., "Touch Prediction for Visual Displays," U.S. Appl. No. 15/191,704, filed Jun. 24, 2016.

* cited by examiner

TOUCH PREDICTION FOR VISUAL DISPLAYS

BACKGROUND

The present disclosure relates to analysis of touch events relating to visual displays, and more specifically, to predicting touch events for a visual display.

Touch screens are used by a growing number of people and for an ever increasing set of applications. The amount of data generated from use of touch screens is also increasing. A particular type of generated data relates to touch events that may be associated with a visual display. This data has the potential to provide a variety of insights about the individuals using the visual display as well as about the visual display itself.

SUMMARY

Various embodiments are directed toward a method for predicting touch events relating to a visual display. The method can include maintaining a database of aggregated touch event history data relative to the visual display and from a plurality of touch screen devices; querying the database according to a set of input parameters defining an environment for use of the visual display; analyzing results from the querying of the database to predict a set of touch events within the environment and based upon inferences obtained from the results; and displaying a representation of the set of touch events with the visual display.

Certain embodiments relate to a method for tracking touch events relating to a visual display. The method can include accessing a plurality of touch event data sets for the visual display, each data set associated with a corresponding electronic device; identifying touch patterns from the touch event data sets; monitoring subsequent touch events by users of the visual display; detecting a match between the touch patterns and subsequent touch events of a particular user of the users; predicting, in response to detecting the match, a possible touch event for the particular user; and modifying, in response to the possible touch event, the visual display for the particular user.

Consistent with embodiments a system can include one or more computer processor circuits and a computer readable storage medium that can have program instructions embodied therewith. The program instructions can executable by the one or more computer processor circuits to cause the system to: maintain a database of aggregated touch event history data relative to the visual display and from a plurality of touch screen devices; query the database according to a set of input parameters defining an environment for use of the visual display; analyze results from the querying of the database to predict a set of touch events within the environment and based upon inferences obtained from the results; and display a representation of the set of touch events with the visual display.

According to embodiments, a computer readable storage medium can have program instructions embodied therewith. The program instructions can executable by the one or more computer processor circuits to cause the system to: maintain a database of aggregated touch event history data relative to the visual display and from a plurality of touch screen devices; query the database according to a set of input parameters defining an environment for use of the visual display; analyze results from the querying of the database to predict a set of touch events within the environment and based upon inferences obtained from the results; and display a representation of the set of touch events with the visual display.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
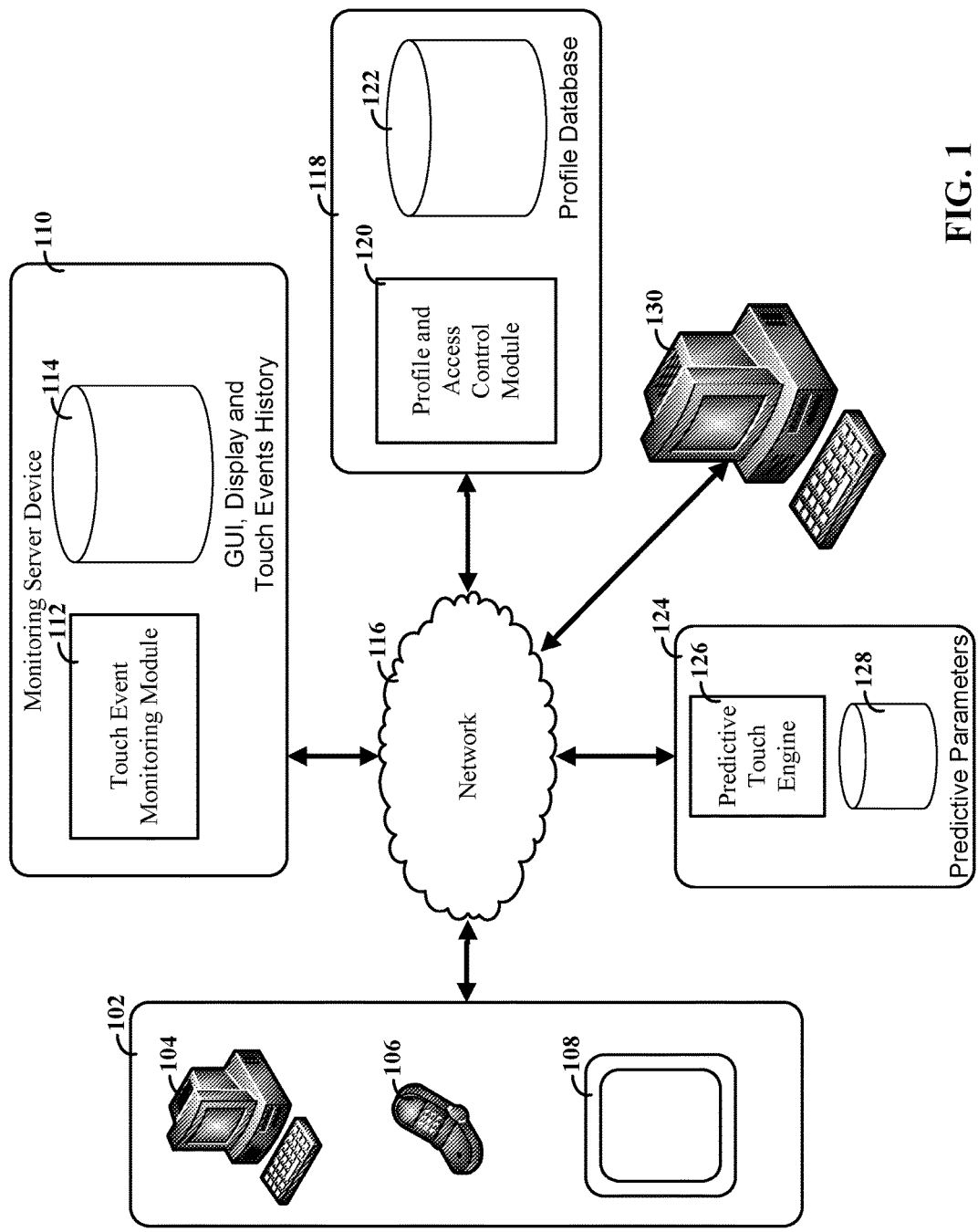
FIG. 1 depicts a block diagram of a system for monitoring and using touch event data for visual displays, consistent with embodiments of the present disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Aspects of the present disclosure relate to analysis of touch events relating to visual displays, more particular aspects relate to predicting touch events based upon touch event histories. While the present disclosure is not necessarily limited to such applications, various aspects of the disclosure may be appreciated through a discussion of various examples using this context.

Various embodiments of the present disclosure are directed toward a system that is configured to monitor touch events relating to a visual display that can be shared with many different individuals using touch screen capable devices. The system can be configured to operate as a cloud based service that collects touch event information from the many different individuals. A database of touch information can be created and then used for a variety of different purposes. For instance, a user of the system can generate a query that specifies a particular environment for using a visual display. Touch event information that has been collected can be used by the system to generate a set of predicted touches for the environment and visual display. The prediction(s) can be presented to the user in a response to the query.

According to embodiments, the viewing experience of one or more individuals can be recreated for a reviewing party. For instance, reviewers can be allowed to see where and how touches occurred with regards to a visual display (e.g., an image or interface). This can include the recreation of viewing experiences based upon sequence of events for a common set of touch sequences. Accordingly, a reviewer can see the recreated view from the vantage point of the individuals that originally used the visual display (e.g., a virtual recreation of how the visual display was used showing each touch and the effect of the touch, whether scrolling, zooming or other action). Consistent with certain embodiments, this recreation can be based upon predicted touch events relating to a query and associated environment.

Certain embodiments are directed toward a system that can determine a set of predicted touches for individuals actively using a visual display. The set of predicted touches can then be used to modify the interactive experience of the individuals in real time. For instance, the system can be configured to proactively highlight, enlarge, or otherwise modify a portion of the visual display that a particular individual is predicted to touch in the future. Other actions are possible, some of which are discussed in more detail herein.

Particular embodiments allow for a variety of different types of additional information to be linked to the touch events being recorded. For example, the additional information may specify dates and times, demographic data of the individual creating the touches, the types of touches (e.g., single touch, double touch, scroll, pinch, multi-touch and others), the capabilities of the touchscreen capable device (e.g., operations system, screen size, or touch screen capabilities). The data can be accumulated using a cloud sourced solution that has the capability to draw touch-based data from a large group of people and over a large period of time. Accordingly, the additional information can be voluminous and varied. Aspects of the present disclosure allow for the data to be accessed using a set of layers or filters that can be applied when using the data for different purposes. For example, if the image associated with the touches is related to the medical field (e.g., a magnetic resonance image (MRI) of an individual), then it may be helpful to filter touches based upon whether the user is a medical professional and further based upon their particular experience level and specialty.

Embodiments of the present disclosure are directed toward generating a prediction of what touch events are likely to occur within a particular set of environment parameters. This can include identifying patterns and correlations between data collected for prior touch events and the particular set of environment parameters. For instance, a machine learning algorithm can be trained using the information collected for prior touch events. The machine learning algorithm can then be used to predict touch events for different sets of environment parameters. For example, the machine learning algorithm can use a supervised learning approach in which the collected data is used to supervise, or train, the algorithm. In certain embodiments, data filtering based upon desired outcomes can be used to further refine the prediction of touch events.

Certain embodiments are directed toward the use of predicted touches to dynamically modify a visual display being actively used by an individual. For instance, environment parameters for a person using a visual display can be collected while they are using the visual display. These parameters can be provided to a prediction engine that analyzes the environment parameters and generates a prediction for future touches of the user using data collected from past users of the same, or similar, user visual display. The predicted touches can then be used to dynamically modify the visual display.

In an example of a dynamic modification, the visual display could be modified to increase the size of the predicted touch area so that it is more easily selected and viewed. Other modifications are also possible, such as increasing highlighting or emphasizing a portion of the visual display. Another possible modification could be responsive to the predicted touch event indicating that the viewing individual is likely to want to view an item that is not currently visible (e.g., that would require scrolling or zooming out). The system can be configured to proactively move the item into current field of view, and thereby, facilitate the use of the visual display. It may also be possible to prefetch data corresponding to predicted touches (e.g., as may be relevant to an interactive interface such as a webpage).

Consistent with embodiments, a visual display modification can include suggested alternatives related to the predicted touch. This may be useful for steering the individual toward a desired use of the visual display, or at least away from an undesired use. The suggested alternatives can also include advertisements that are correlated to the predicted touch events (e.g., if the touch event suggests interest in a particular item shown by the visual display, relevant advertisements can be displayed).

Various aspects of the present disclosure are directed toward facilitating analysis and review of visual displays and their usage. For instance, a visual display containing one or more medical images (e.g., X-ray or MRI) and diagnostic graphs or charts (e.g., electrocardiography (ECG)) can be shared with a community of doctors or other individuals, and touch event data can be collected. A reviewing individual (e.g., a professional treating a patient corresponding to the images or charts) can use the recorded touch data to identify points of interest indicated by the community, glean information about the analysis process of others, and for other purposes. The system can also be configured to allow the reviewing individual to setup and apply various filters on the data. In the medical example, the reviewing individual could filter based upon doctor experience or specialty. The results of different filter could also be compared to assess the differences.

In various embodiments, a predictive touch engine can be used in facilitating analysis and review of visual displays and their usage. For example, a reviewing individual can submit a query to the system in order to predict what touch events would occur in certain situations, which can be defined in terms of environment parameters. As an example, the reviewing individual may desire predictive information regarding a website and a particular demographic of users. The predictive engine can make inferences to determine a set of likely touches for the demographic based upon touch data collected from past users of the website. In this manner, the reviewer can obtain useful information about likely use of the website even for a set of demographics for which there is little or no touch data.

Consistent with various aspects of the present disclosure, the system can allow for sharing of information in combination with the recorded touch events. For example, individuals using the visual display can choose to add annotations (e.g., text, audio or video) to touch events. In the medical environment, for instance, doctors could touch a point of interest on an image or chart and add in notes regarding the significance. The consolidated set of touch events and annotations can then be reviewed and assessed by the source of the images or charts.

Turning now to the figures, FIG. 1 depicts a block diagram of a system for monitoring and using touch event data for visual displays, consistent with embodiments of the present disclosure. The system of FIG. 1 can be configured to monitor touch events originating from user devices 102, which can each have touch screen capabilities. The user devices can include, but are not necessarily limited to, personal computers 104, smart phones 106 and tablet devices 108. For example, the user devices 102 can obtain the visual display over a network 116 and then display the visual display using a touch screen. A local module can be initiated on the user device in order to monitor and record touch event data that corresponds to the use of the visual display. In particular embodiments, the local module can be configured to store touch event information substantially independent from active components (if any) of the visual display. For example, the visual display could be a photograph or other image without any intrinsic active selection components (e.g., as opposed to an active website with selectable buttons, links or other interactive components).

According to certain embodiments, the local module can be configured to transmit the touch event data to a touch event monitoring module 112. The touch event monitoring module 112, and other modules and engines discussed herein, can be stored on a computer readable medium as instructions that are configured to run on one or more processor circuits corresponding to one or more monitoring server devices 110. The touch event data can then be stored in a database 114, which can aggregate information from a large number of potential users over a period of time. The resulting touch event history can also include additional information relating to the environment of the touch events (e.g., user demographics, time, or geographic location).

A reviewer, or administrator, of the visual display can access the system using a computer device 130. The system can include a server device 118 that provides a profile and access control module 120. The access control module 120 can be configured to control access to the touch event history data and to allow for customizations for different reviewers based upon information stored in a profile database 122. The profile and access control module 120 can also handle security and verification of a reviewer or administrator (e.g., using user login and password checks or other verifications methods). For instance, each reviewer can be authorized to access data for a set of one more displays that they can provide and control. The profile and access control module 120 can verify the identity of an individual using a computer device 130 and then allow access to portions of the touch event history database 114 that correspond to the set of displays for the identified individual. Other information can be stored such as user preferences regarding previously used filters and environmental parameters.

In addition to accessing the data stored in the touch event history database 114, the computing device 130 can generate queries for predictive touch information. These queries can be sent to a server device 124 that can be configured to include a predictive touch engine 126. The predictive touch engine can be configured to respond to a query by analyzing data stored in touch event history database 114 according to the query parameters and appropriate predictive parameters 128. In certain embodiments, predictive touch engine 126 can train a machine learning algorithm from data in the touch event history database 114. The training can be visual display specific and it can also include training across multiple visual displays. The results of the training can be stored in the predictive parameters database 128. When a query request for predictive touches for a visual display with certain environmental parameters is received, the predictive touch engine can apply the learning algorithm using the appropriate predictive parameters. The resulting set of predictive touches can then be provided to satisfy the query.

Various embodiments allow for queries to be generated automatically and for the predictive touch events for the query to be used in dynamic and real time applications. For example, a visual display could be part of a website for which touch event data has been collected over a period of time and for which the predictive touch engine is configured to generate predictive touch event data. When a new user accesses the website, the touch event monitoring module 112 can send queries to the predictive touch engine using environmental parameters matching the browsing session of the new user. The predictive touches returned as part of the queries can then be used to modify the viewing experience of the new user. This can include, but is not limited to, highlighting portions of the visual display that are likely to be touched, changing the size of portions of the visual display, automatically scrolling a portion of the display, customizing advertisements and prefetching data expected to be needed due to a predicted set of touches.

Figure 2:
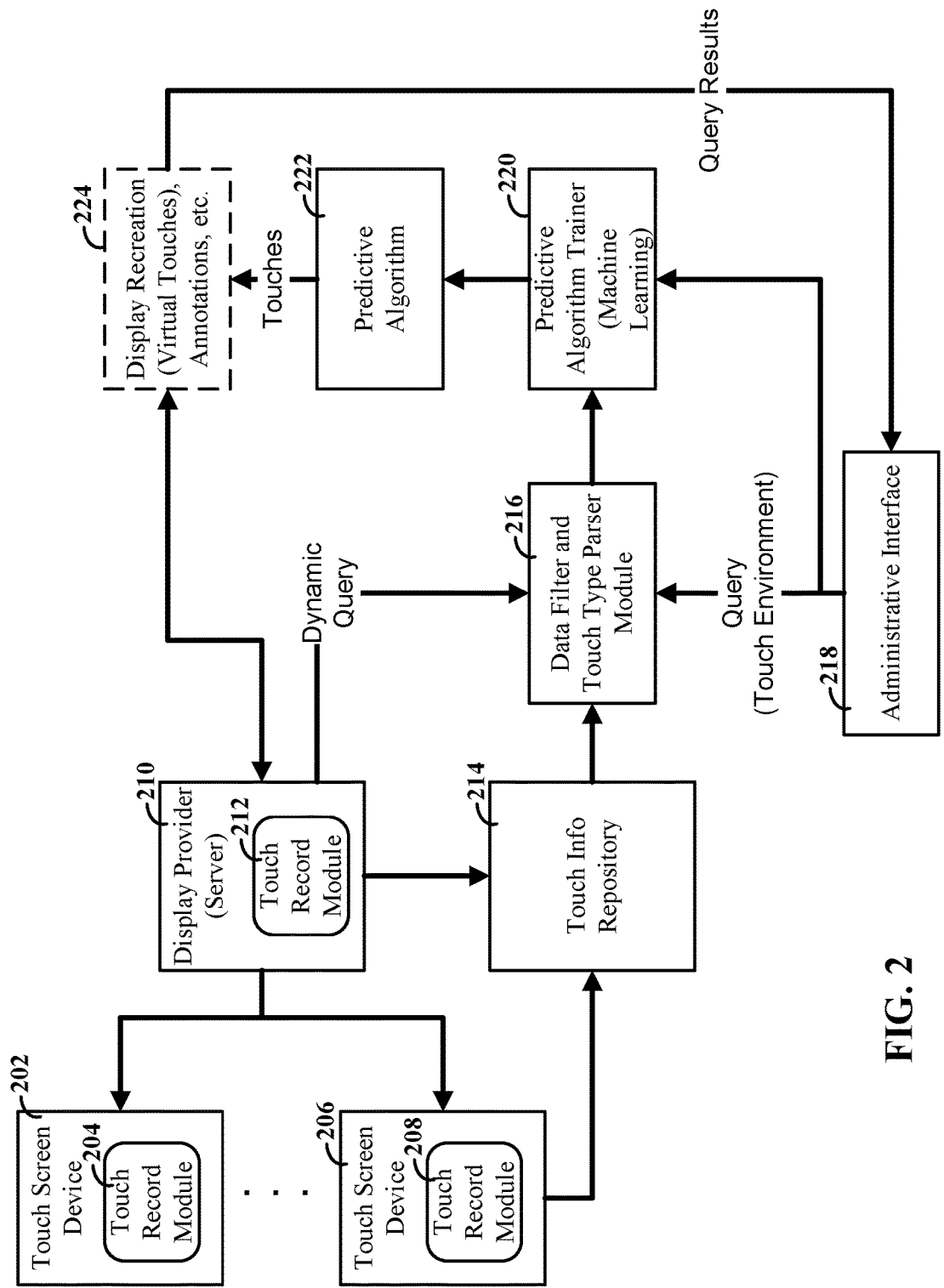
FIG. 2 depicts a flow diagram of a system for monitoring and using touch event data associated with a visual display, consistent with embodiments of the present disclosure.

FIG. 2 depicts a flow diagram of a system for monitoring and using touch event data associated with a visual display, consistent with embodiments of the present disclosure. Touch screen devices 202, 206 can be configured to include a touch record module 204, 208. The touch record module 204, 208 can monitor touch events associated with one or more visual displays. The visual displays can be provided by a display provider 210. Display provider 210 can include one or more computers or servers that are accessible over a network, such as the global Internet. Consistent with certain embodiments, display provider 210 can also provide a touch record module 212 for download by touch screen devices. The display provider 210 can also use a version of a touch record module 212 that collects touch event data from touch screen devices 202, 206.

For instance, a touch record module 204, 208 can be installed by a user of a touch screen device, whether from display provider 210 or from other sources. The user can expressly initiate the touch record module 204, 208 when using a visual display for which touch event data is relevant, or the module can be automatically initiated upon detecting that a valid visual display is accessed. In certain embodiments, the module can be downloaded and initiated in response to accessing a remotely provided visual display. For example, the module can be run as an embedded application operating within a web browser application.

Consistent with various embodiments, the touch record modules 204, 208 can be configured to allow a user to enable or disable the recording feature depending upon their preference. The modules can also be configured to allow a user to add additional information with touch events, such as adding text or audio to a touch point. As an example, a doctor could touch a portion of a visual display and select an annotation option provided by touch record module 204, 208. The additional annotation material added by the doctor can then be provided for storage in a touch information repository or database 214, along with the touch event indications.

According to embodiments, an administrative interface 218 can be provided to reviewers and administrators of the visual displays. The interface can be designed to allow the reviewers to generate queries regarding visual displays and touch event history data. For example, a reviewer may seek information regarding a particular set of environmental parameters. As an example, a reviewer of a visual display that is part of a website might create a query with the environmental parameters that include demographic information for users and touch screen capabilities (e.g., screen resolution). The parameters might be selected in order to understand usage patterns and identify potential problems with the website use and flow.

Queries from the administrative interface 218 can be provided to a data filter and touch type parser module 216 (hereafter referred to as a "data filter module"). The data filter module 216 can filter data based upon the query parameters. This can include filtering touch event history data based upon the particular visual display(s) for the query and based on various environmental parameters. For example, a reviewer seeking medical-based data could generate a query that filters data based upon experience and specialty of the source of the touch events. The data filter module 216 can also be configured to parse touch event data according to the type of touch. This can include identifying touch events such as zoom (in or out), scroll, double touches and others. Touches can then be parsed and associated according to these identified touch event types. In certain embodiments, this type of parsing can be done before data is stored in the touch information repository or database 214.

In various embodiments, the touch data history can be used by a predictive algorithm trainer 220 to train parameters used by a predictive algorithm 220 based upon data from the touch info repository 214. In certain embodiments, the training can be carried out using filtered and parsed data 216. Various embodiments also contemplate training being carried out using unfiltered data, which might also be carried out before queries are received.

The trained parameters can be used by predictive algorithm 222 to generate a set of predictive touches for the query and associated environmental parameters. The predicted touches can then be provided along with the visual display from the display provider 210 to satisfy the query from administrative interface 218. In certain embodiments, the predicted touch events can be provided to a display recreation module 224. Display recreation module can be configured to generate a replication of what a user would see relative to the touch environment in the query and in response to the predicted touch events. For example, the predicted touch events may include a sequence of zooming and repositioning touches that can be recreated so that the reviewer can see what a user would be viewing while the touch events are carried out.

Consistent with various embodiments, the system can be designed to allow a reviewer to also review touch event history directly (e.g., with or without the use of predictive touch events). This ability can be used in connection with express annotations and input from the generators of the touch event history. Particular embodiments allow a review to identify a source of particular touch events or annotations and elicit further information from the identified source. For example, a reviewing doctor may seek further details regarding their technique for analyzing a display or their reason for focusing on a particular item.

Various embodiments also allow for users of the visual display to view comments and touch events of other users. For example, participant voting and additional comments can be used to further refine shared experience (e.g., doctors may disagree with one comment and vote down and/or add contrary input). The results of this collaborative effort can be provided to the reviewers and to the participants.

As discussed herein, embodiments of the present disclosure allow for queries to be generated dynamically and for the resulting predictive touches to be used to modify the visual display in real time. For example, the visual display provider server 210 can be configured to generate dynamic queries for users actively using a visual display, such as a website. The results of the query can be provided back to the visual display provider server 210 and used to improve the viewing experience of the users by dynamically modifying the visual display during its use.

Figure 3:
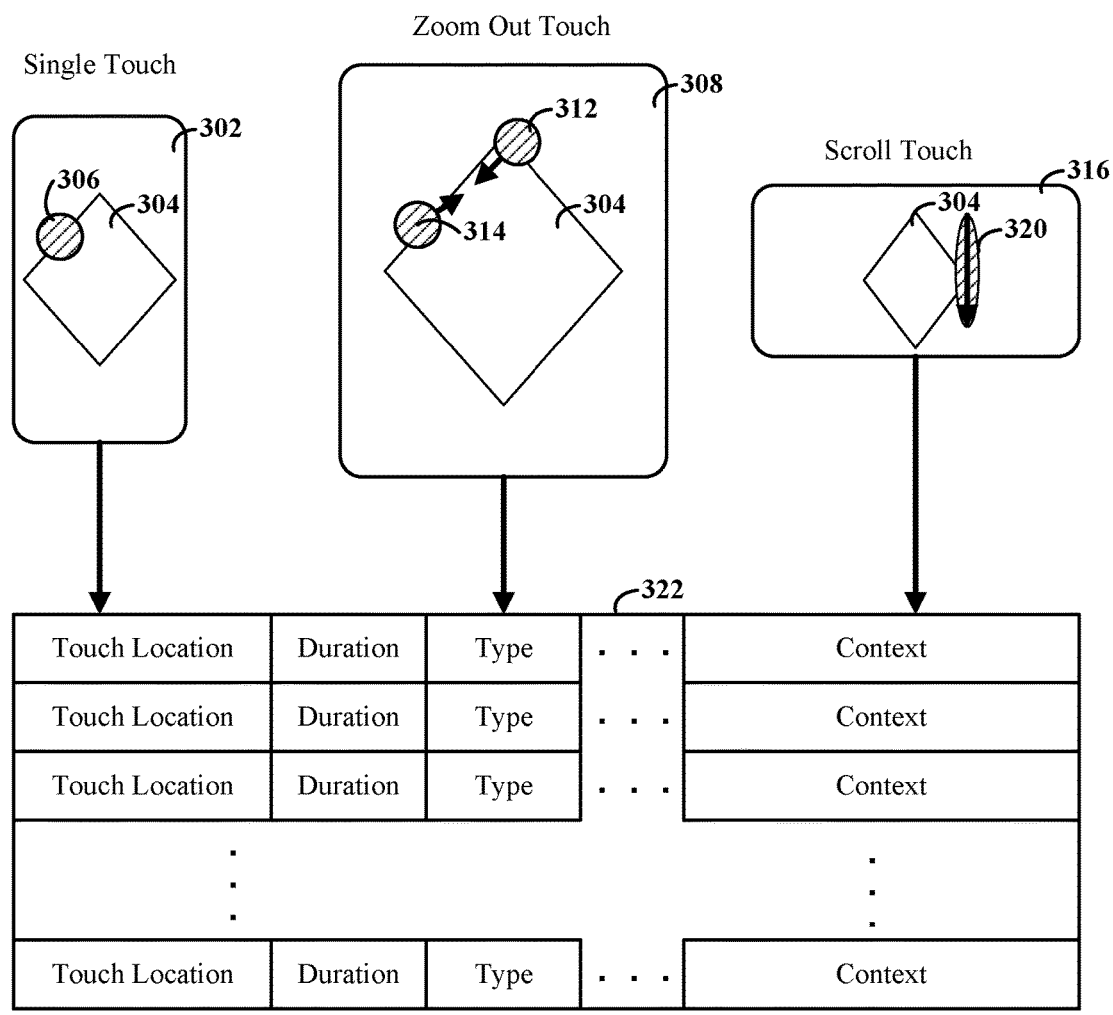
FIG. 3 depicts a set of different example touch events for different devices and a resulting database table, consistent with embodiments of the present disclosure.

FIG. 3 depicts a set of different example touch events for different devices and a resulting database table, consistent with embodiments of the present disclosure. Displays 302, 308 and 316 depict different example screen sizes and orientations that might be used to show a visual display containing an element 304. The visual display is shown as including element 304 that is a simple diamond for illustrative purposes. The visual display, however, can include a variety of complex and different elements, including but not necessarily limited to, text, selectable icons, dropdown menus, images, embedded videos, and animated images.

Display 302 shows rectangular display screen with a horizontal (portrait) orientation and as single touch event 306. Display 308 shows a wider display screen having two touch points 312 and 314 that also include motion indicated by the arrows. This type of touch event may indicate that the user zoomed out to view more of the visual display. Display 316 shows another rectangular display screen that is in a vertical (landscape) orientation. A touch even 320 is indicated with a downward motion component shown by an arrow. This type of motion may indicate repositioning or scrolling was done by the user.

Consistent with embodiments of the present disclosure, the touch events for the different devices can be stored in a database or repository 322. Non-limiting examples of data that can be stored in the repository include touch location (e.g., XY coordinates referenced to the visual display), touch duration, touch motion, touch type (if parsing is done prior to queries), and touch context (including data implicitly or explicitly provided by a user).

Figure 4:
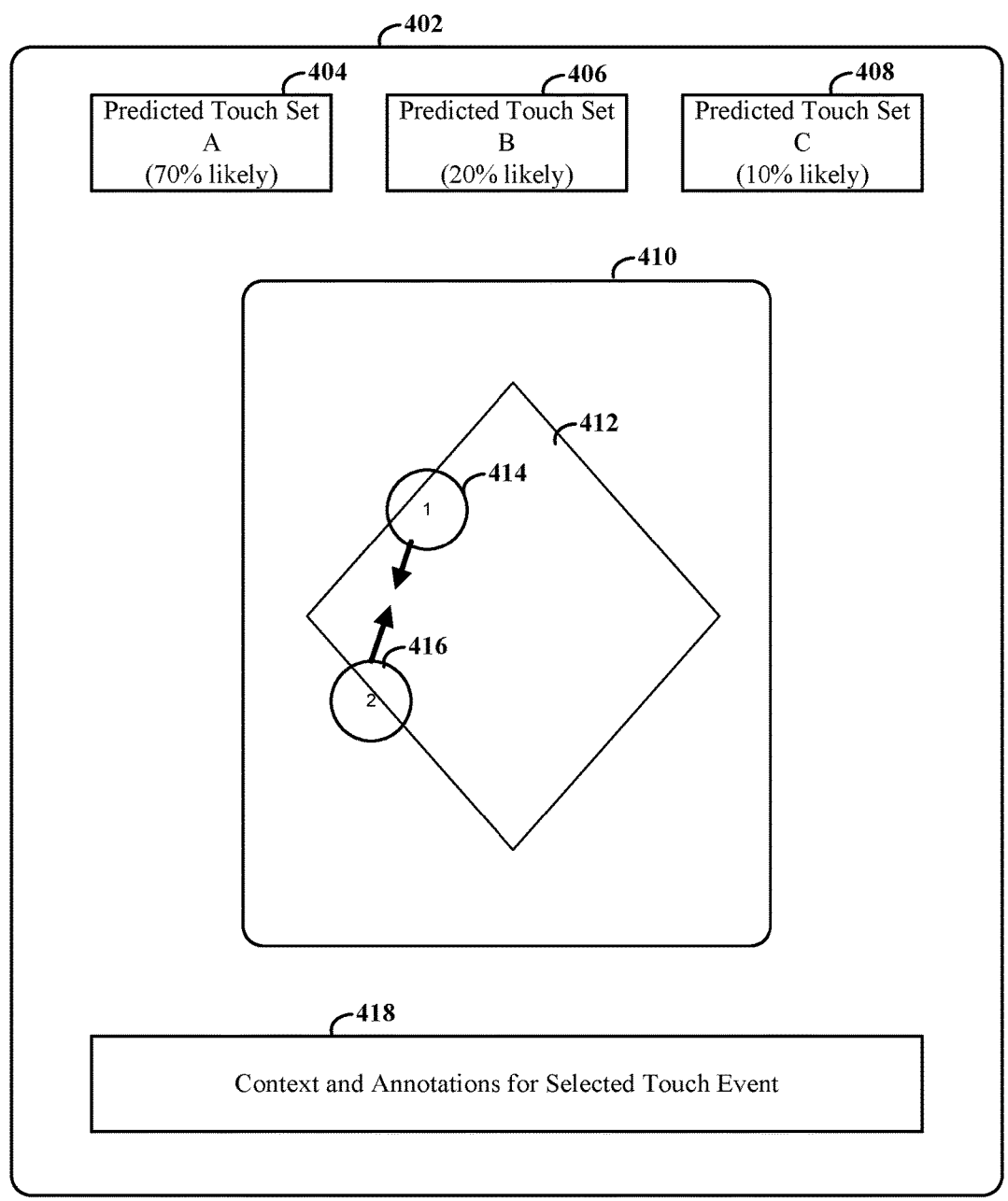
FIG. 4 depicts an interface that can be viewed by a reviewer or administrator, consistent with embodiments of the present disclosure.

FIG. 4 depicts an interface that can be viewed by a reviewer or administrator, consistent with embodiments of the present disclosure. Interface 402 can be provided using an administrative interface (e.g., as discussed in connection with FIG. 2). Display portion 410 can recreate the visual display, having one or more display elements 412, within the environment associated with the query. For example, the environment may specify a touch screen size and resolution. The predicted touch events 414, 416 can be shown on the display portion. Additional information for the predicted touch events can also be displayed. This may include motion associated with the touch events, as indicated by the arrows (other ways of showing motion are possible), and context and annotations 418. The context and annotations 418 can change depending upon which touch events are selected by the reviewer.

In certain embodiments, the predictive engine can generate multiple sets of predicted touch events that each have a different predictive likelihood of occurring. These different sets are displayed in selectable boxes 404, 406, 408 that can include a probability percentage indicating how likely each set is to occur. For example, a touch set A (404) can be determined to be 70% likely to occur, a touch set B (406) can be determined to be 20% likely, and a touch set C (408) can be determined to be 10% likely. The interface 402 can present this information in a variety of manners, which can be selected by the reviewer. For instance, the different touch event sets can be displayed when selected by the reviewer. This may allow for individual review of each or for multiple touch sets to be displayed simultaneously.

Figure 5:
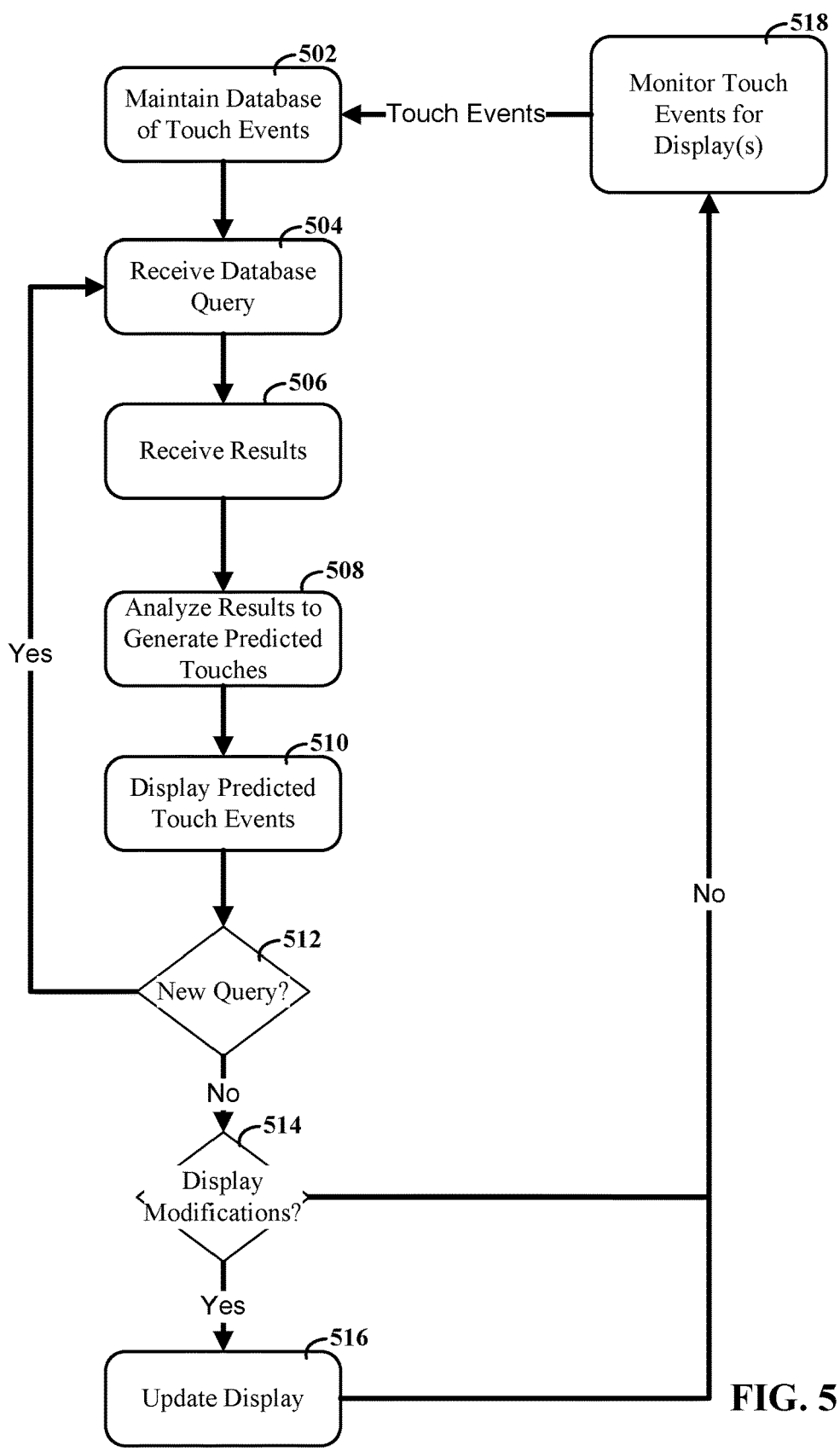
FIG. 5 depicts a process flow for using touch event history data to generate predictive touch event sets, consistent with embodiments of the present disclosure.

FIG. 5 depicts a process flow for using touch event history data to generate predictive touch event sets, consistent with embodiments of the present disclosure. A touch monitoring system can be configured to generate and maintain a database of aggregated touch event history data relative to the visual display and from a plurality of touch screen devices, as shown by block 502. This can include the use of various touch monitoring modules and collecting and aggregating data from a large number of potential user devices using a shared pool of configurable computing resources.

The maintained database can then be queried according to a set of input parameters defining an environment for use of the visual display, per block 504. This may include an environment that is defined in terms of parameters such as time of year or day, viewing device capabilities, user demographics, geographic location of viewing device, and connection bandwidth.

The results of the query of the database can then be received, per block 506, and then analyzed and used to predict a set of touch events within the environment and based upon inferences obtained from the results, per block 508. For example, the environment may specify a set of parameters for which there is little or no direct touch event history. Accordingly, a predictive algorithm can be used to infer likely touch events from touch event history from similar environments.

Consistent with embodiments, the predictive touch events can be provided to the query source (e.g., reviewer) using a representation of the set of touch events with the visual display, per block 510. This may include displaying the visual display with shading or other indications of where the predicted touch events are located on the display.

Embodiments allow for multiple different queries to be generated and serviced, accordingly the system can determine whether or not there are additional or new queries, per block 512. If there are new queries, the system can query the database, per block 504, and then repeat the process flow described above. If there are not any new queries, then the system can continue to monitor touch events, per block 518 and maintain the database per block 502.

In certain embodiments, the system can be configured to determine whether or not to use information from the predictive touch events to update or modify the visual display, per block 514. This can include modifications that are automatically carried out (such as real time modifications made while a user is accessing a website with the visual display) or in response to input from a reviewer. If it is determined that the display is to be updated, then the system can carry out the changers per block 516.

Figure 6:
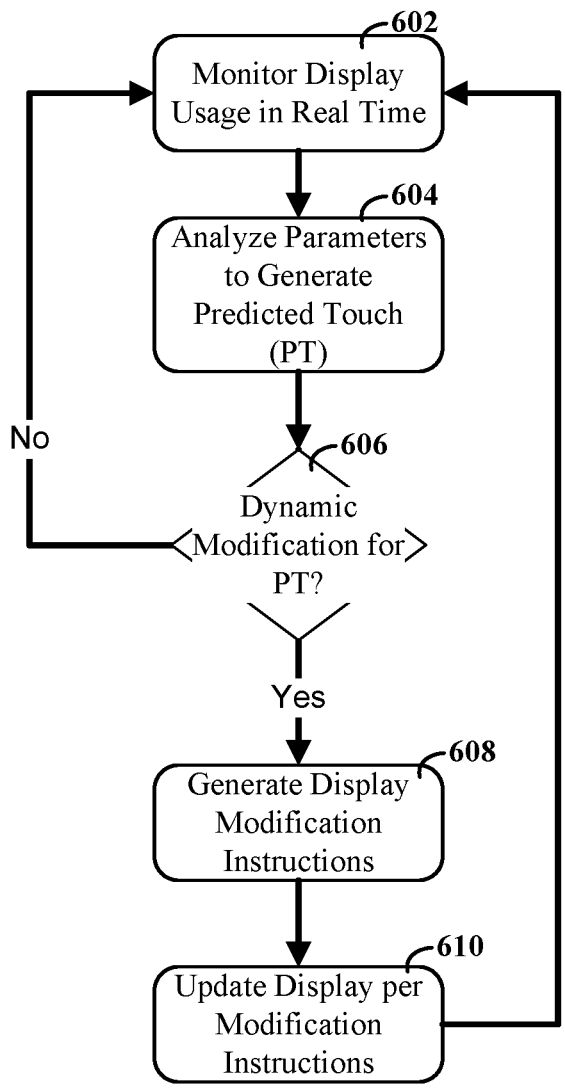
FIG. 6 depicts a flow diagram for a system that can dynamically modify a visual display, consistent with embodiments of the present disclosure.

FIG. 6 depicts a flow diagram for a system that can dynamically modify a visual display, consistent with embodiments of the present disclosure. The system can monitor the display usage, per block 602. For example, the user selections and touch events can be monitored and recorded as the user is accessing the visual display, such as a website. The system can then analyze the monitored data and learned touch parameters to generate a set of predicted touches for the user, per block 604. As discussed herein, the parameters can be developed from training of a machine learning algorithm from past touch event data that has been collected and analyzed.

The system can then determine whether or not the predicted touches signify that a modification to the visual display is warranted, per block 606. For example, the predicted touches may indicate that the user is likely to zoom into a particular portion of the visual display. This sort of action can be flagged to indicate a modification is necessary (e.g., in order to proactively enlarge the particular portion). Other triggering predicted touches are also possible. If no modification is indicated, the system can continue to monitor the visual display usage, per block 602. If a modification is indicated, the system can generate a set of display modification instructions, per block 608. The visual display can then be updated, as shown by block 610.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
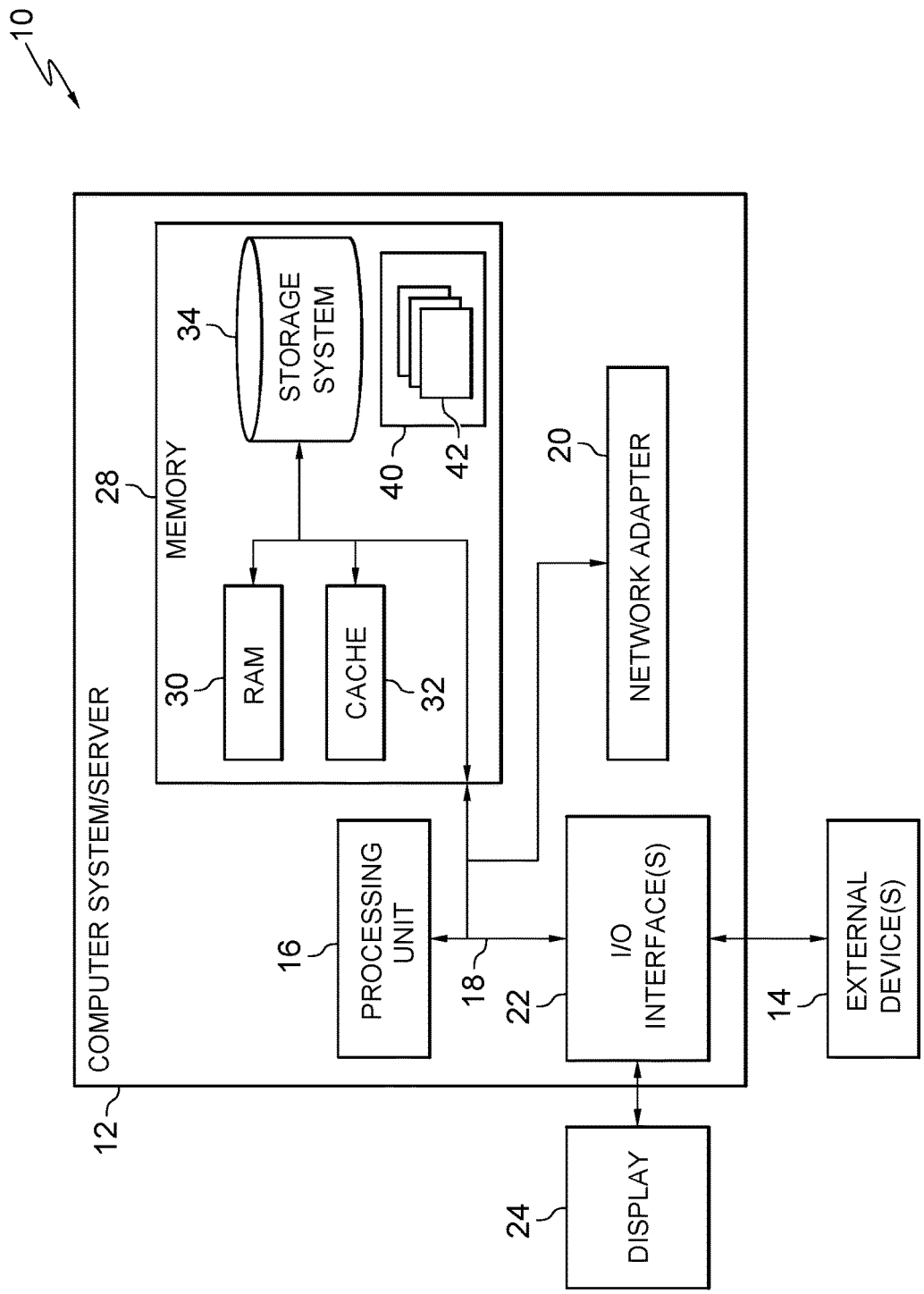
FIG. 7 depicts a cloud computing node, according to an embodiments of the present disclosure.

Referring now to FIG. 7, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 8:
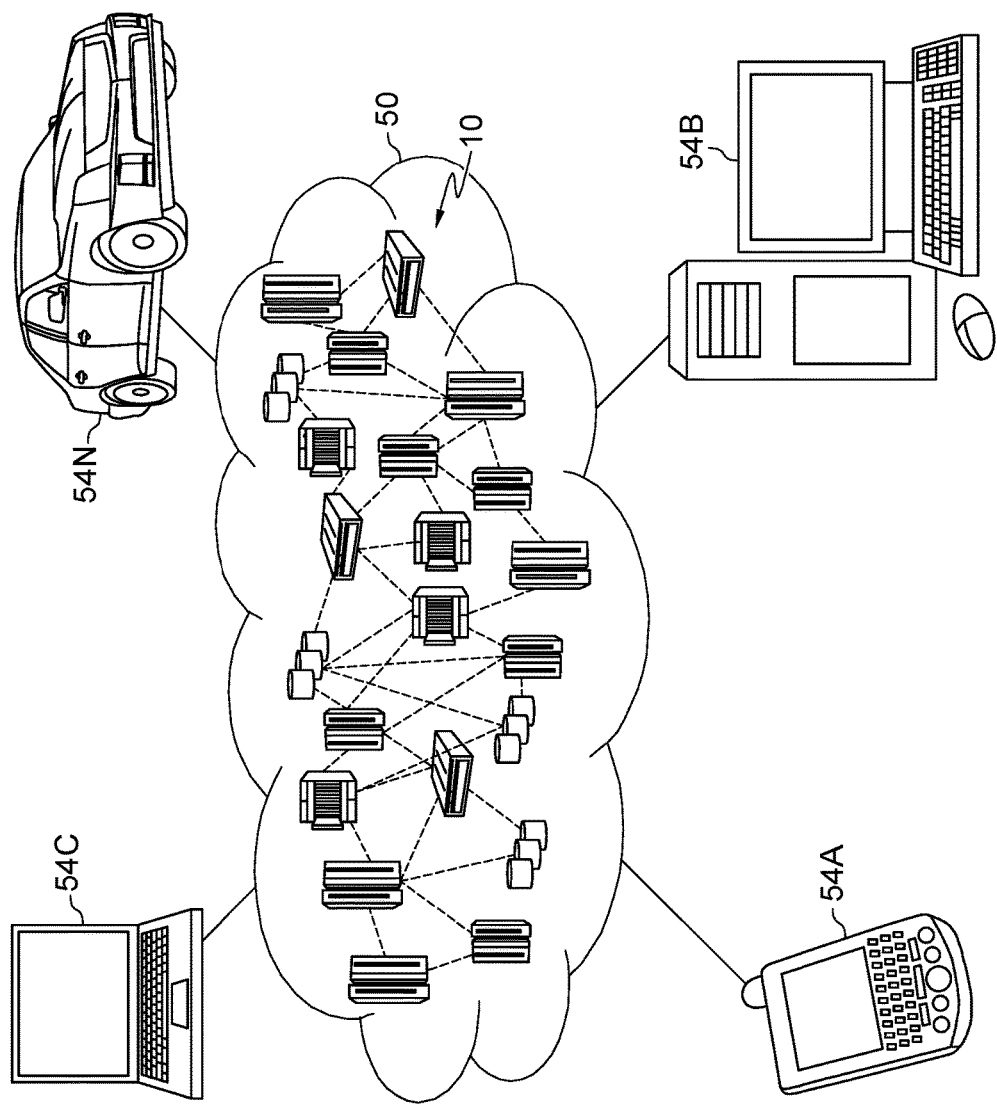
FIG. 8 depicts a cloud computing environment, according to embodiments of the present disclosure.

Referring now to FIG. 8, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 8 are intended to be illustrative only and that computing nodes 10 and cloud computing environment 50 can communicate with any type of computerized device over any type of network and/or network addressable connection (e.g., using a web browser).

Figure 9:
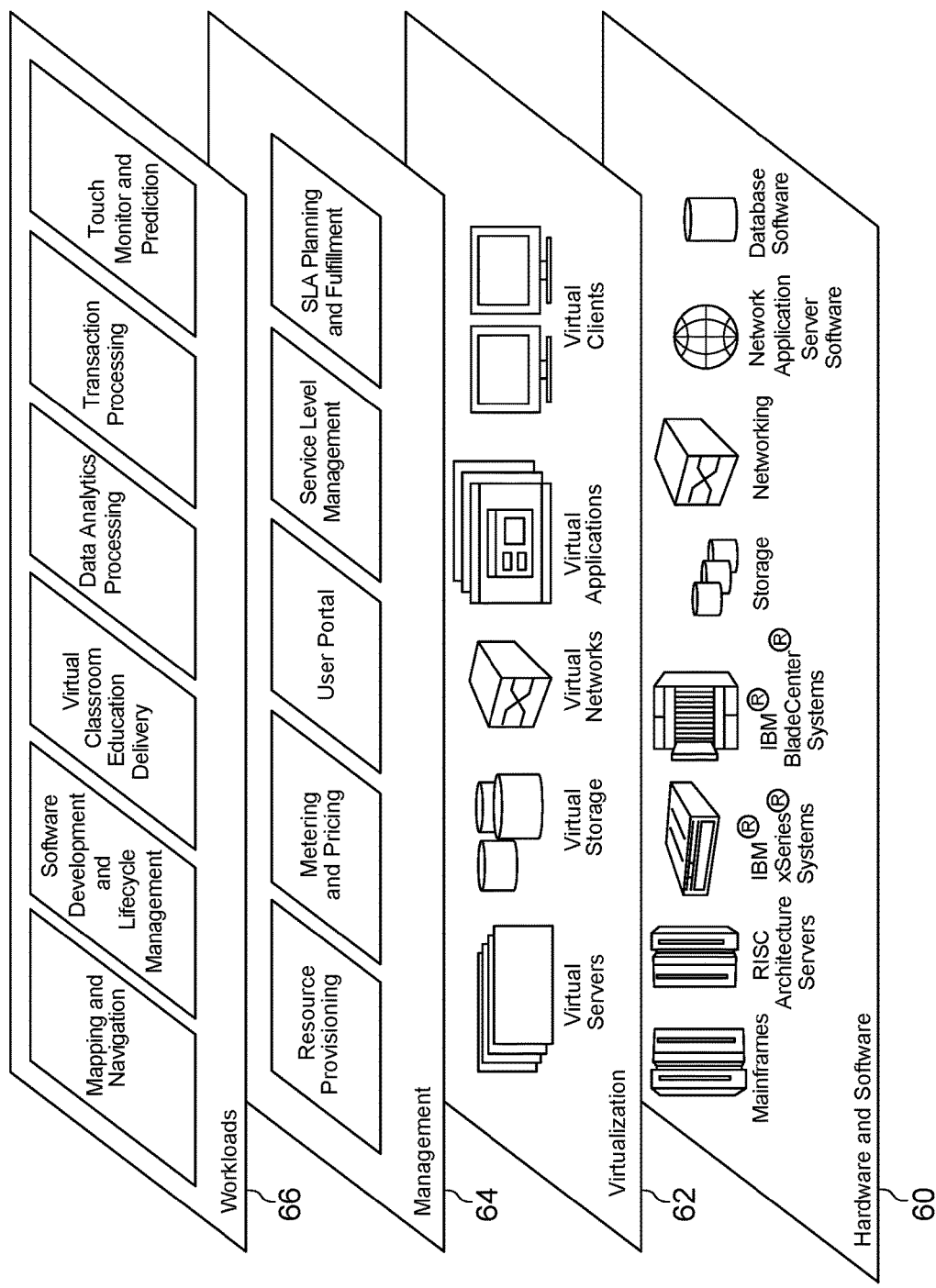
FIG. 9 depicts abstraction model layers, according to embodiments of the present disclosure.

Referring now to FIG. 9, a set of functional abstraction layers provided by cloud computing environment 50 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 62 provides an abstraction layer from which the following examples of virtual entities may be provided: virtual servers; virtual storage; virtual networks, including virtual private networks; virtual applications and operating systems; and virtual clients.

In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; and transaction processing; and mobile desktop.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A method for tracking touch events relating to a visual display on a first electronic device, the method comprising:
    identifying a set of environmental parameters, wherein the environmental parameters provide information regarding an environment in which the visual display is used on the first electronic device by a user;
    accessing a plurality of touch event data sets for the visual display, the plurality of touch event data sets corresponding to the environmental parameters and associated with the visual display as used on at least a second electronic device;
    identifying touch patterns from the plurality of touch event data sets;
    monitoring subsequent touch events by the user of the visual display;
    detecting a match between the touch patterns and the subsequent touch events of the user;
    predicting, in response to detecting the match, a possible touch event for the user, wherein the predicting the possible touch event indicates that the user is likely to perform the possible touch event and wherein the user has not previously performed the possible touch event; and
    modifying, in response to the possible touch event, the visual display on the first electronic device for the user, wherein the modifying automatically updates the visual display as if the user had performed the possible touch event on the visual display.

2. The method of claim 1, wherein the touch event data sets specify sequences of touch events, touch coordinates relative to the visual display and different types of touch events.

3. The method of claim 1, wherein modifying the visual display includes moving an item into a field of view of the visual display.

4. The method of claim 1, wherein modifying the visual display includes displaying touch event data of other users.

5. The method of claim 1, wherein the touch patterns comprise at least one touch event performed on a visual display that lacks an interactive component.

6. A system comprising:
a processor; and
a memory in communication with the processor, the memory containing program instructions that, when executed by the processor, are configured to cause the processor to perform a method for tracking touch events relating to a visual display on a first electronic device, the method comprising:
identifying a set of environmental parameters, wherein the environmental parameters provide information regarding an environment in which the visual display is used on the first electronic device by a user;
accessing a plurality of touch event data sets for the visual display, the plurality of touch event data sets corresponding to the environmental parameters and associated with the visual display as used on at least a second electronic device;
identifying touch patterns from the plurality of touch event data sets;
monitoring subsequent touch events by the user of the visual display;
detecting a match between the touch patterns and the subsequent touch events of the user;
predicting, in response to detecting the match, a possible touch event for the user, wherein the predicting the possible touch event indicates that the user is likely to perform the possible touch event and wherein the user has not previously performed the possible touch event; and
modifying, in response to the possible touch event, the visual display on the first electronic device for the user, wherein the modifying automatically updates the visual display as if the user had performed the possible touch event on the visual display.

7. The system of claim 6, wherein the touch event data sets specify sequences of touch events, touch coordinates relative to the visual display and different types of touch events.

8. The system of claim 6, wherein modifying the visual display includes moving an item into a field of view of the visual display.

9. The system of claim 6, wherein modifying the visual display includes displaying touch event data of other users.

10. The system of claim 6, wherein the touch patterns comprise at least one touch event performed on a visual display that lacks an interactive component.

11. A computer program product, the computer program product comprising a computer readable storage medium having program instructions embodied therewith, the program instructions executable by a computer to cause the computer to track touch events relating to a visual display on a first electronic device, the tracking comprising:
identifying a set of environmental parameters, wherein the environmental parameters provide information regarding an environment in which the visual display is used on the first electronic device by a user;
accessing a plurality of touch event data sets for the visual display, the plurality of touch event data sets corresponding to the environmental parameters and associated with the visual display as used on at least a second electronic device;
identifying touch patterns from the plurality of touch event data sets;
monitoring subsequent touch events by the user of the visual display;
detecting a match between the touch patterns and the subsequent touch events of the user;
predicting, in response to detecting the match, a possible touch event for the user, wherein the predicting the possible touch event indicates that the user is likely to perform the possible touch event, and wherein the user has not previously performed the possible touch event; and
modifying, in response to the possible touch event, the visual display on the first electronic device for the user, wherein the modifying automatically updates the visual display as if the user had performed the possible touch event on the visual display.

12. The computer program product of claim 11, wherein the touch event data sets specify sequences of touch events, touch coordinates relative to the visual display and different types of touch events.

13. The computer program product of claim 11, wherein modifying the visual display includes moving an item into a field of view of the visual display.

14. The computer program product of claim 11, wherein modifying the visual display includes displaying touch event data of other users.

15. The computer program product of claim 11, wherein the touch patterns comprise at least one touch event performed on a visual display that lacks an interactive component.

* * * * *